United States Patent [19]

Koike

[11] Patent Number: 4,974,458

[45] Date of Patent: Dec. 4, 1990

[54] AUTOMATIC PREPARATION APPARATUS AND SUPPORT ARM

[75] Inventor: Toshio Koike, Kawasaki, Japan

[73] Assignee: Ajinomoto Company, Inc., Tokyo, Japan

[21] Appl. No.: 382,202

[22] Filed: Jul. 19, 1989

Related U.S. Application Data

[63] Continuation-in-part of Ser. No. 282,552, Dec. 12, 1988.

[30] Foreign Application Priority Data

| Dec. 14, 1987 | [JP] | Japan | 62-189809 |
| Dec. 14, 1987 | [JP] | Japan | 62-315793 |
| Oct. 19, 1988 | [JP] | Japan | 63-263526 |
| May 17, 1989 | [JP] | Japan | 1-56878 |

[51] Int. Cl.$^5$ .............................................. G01N 1/34
[52] U.S. Cl. .................................................. 73/864.025
[58] Field of Search ........................ 73/863.23, 863.25, 864.21–864.25;
422/64, 65, 70, 100; 210/435, 437–439, 445, 446, 451

[56] References Cited

U.S. PATENT DOCUMENTS

| 3,085,689 | 4/1963 | Hering et al. | 210/445 |
| 3,484,206 | 12/1969 | Loebl | 422/64 |
| 3,748,905 | 7/1973 | Fletcher et al. | 73/863.25 |
| 4,167,875 | 9/1979 | Meakin | 73/863.25 |
| 4,170,625 | 10/1979 | Welch | 422/64 |
| 4,430,213 | 2/1984 | Ishikawa | 210/445 |
| 4,836,038 | 6/1989 | Baldwyn | 422/64 |
| 4,841,786 | 6/1989 | Schulz | 73/864.25 |

FOREIGN PATENT DOCUMENTS

| 0211155 | 2/1987 | European Pat. Off. . |
| 61-64308 | 4/1986 | Japan . |
| 61-69142 | 4/1986 | Japan . |
| 251242 | 8/1969 | U.S.S.R. | 73/863.25 |

OTHER PUBLICATIONS

Patent Abstracts of Japan, vol. 11, No. 226 (P-598) [2673], 23rd Jul. 1987; and JP-A-62 42 063 (Sumitomo Chem. Co.) 24-02-1987.

*Primary Examiner*—Robert Raevis
*Attorney, Agent, or Firm*—Oblon, Spivak, McClelland, Maier & Neustadt

[57] ABSTRACT

An automatic preparation apparatus has turntable means in which a plurality of test tubes can be disposed in radial direction, filter robot means which can move a releasable filter onto one of those test tubes, and probe robot means which can sample the liquid contained within one of the test tubes and inject a predetermined amount of liquid into another one of the test tubes and filter. Furthermore, the apparatus comprises control means for controlling those means in accordance with a predetermined sequence to effect a desired preparation. The probe robot means has a support arm member for supporting the filter. The support arm member includes a head section having a filter retainer mechanism for releasably retaining the filter and a sealing mechanism for forming a sealing chamber on a sample-injecting side of the filter, an arm section having an end tip portion connected to the head section and a rear end portion attached to a support post member, and a device for detachably connecting the head section to the arm section.

14 Claims, 13 Drawing Sheets

AUTOMATIC PREPARATION APPARATUS AND SUPPORT ARM

CROSS-REFERENCE TO RELATED APPLICATION

This application is a continuation-in-part application of Ser. No. 07/282,552, filed on Dec. 12, 1988, now pending.

BACKGROUND OF THE INVENTION

1. Field of the Invention

The present invention relates to an automatic preparation apparatus for automatically preparing samples and a support arm. The apparatus automatically performs the preparations such as filtration, dilution, reaction of suspensions and solutions containing chemical substances.

2. Description of the Related Art

When a sample is injected in the component analysis, suspended matters contained within the sample are usually previously removed to dilute it to a predetermined concentration. Centrifugal separator or filter is used for removing the suspended matters from the sample while a measuring pippet is used for diluting the sample. For example, when a (high speed) liquid chromatography system is used to perform the component analysis, neither of the above-mentioned removing and diluting means can directly be coupled with the liquid chromatography system for operational reasons and thus the prepared sample is set to an automatic sampler or is injected into an injector by means of a microsyringe.

Consequently, liquid chromatography system cannot be run fully automatically including regulation to analysis of the sample and those treatments of the sample are currently being manually carried out.

However, if the preparations are to be manually carried out, a vast amount of treatment time can be required, not to say of the possible occurrence of the treatment error and contamination of the sample. Besides, a problem exits that the preparation and component analysis by the liquid chromatography system cannot automatically be controlled in an interlocking relations. Furthermore, when the sample is to be filtered by means of the preparing apparatus of this kind, filtration speed of the sample can thereby by retarded or pores of the filter medium can be clogged depending on the kind or size of the inclusions existing within this sample such as bacteria, fiber, fine particles or the like. In such cases, for ease and effective control of the filtration, it is necessary to simultaneously use the proper filter or filter aid.

However, in the case of the currently commercially available or proposed disposable molded filters, since the inner diameter of a portion into which the sample to be filtered may be injected ranges about below 4 to 5 mm, it is difficult to use, as the occasion demands, the other filter, filter as described above, which in turn resulted in slow filtration speed of the sample and a large amount of time required for obtaining enough filtrate to analyze.

By using a disposable filter, it is not necessary to clean the filter since the filter is detachable and thrown away, but it is necessary to clean a filter support arm for attaching this filter thereto with respect to the liquid attached to the support arm in the filtering processing. However, in the conventional apparatus of this kind, it is impossible to easily diassemble and detach a head section of the support arm therefrom so that the entire support arm cannot be cleaned with respect to the liquid attached thereto. When the liquid attached to the support arm cannot be completely removed therefrom, this liquid is mixed with a new liquid at the next filtering processing time. Therefore, there is a fear that the attached liquid is solidified and thereby a mechanism for attaching and detaching the filter is unoperated, etc.

SUMMARY OF THE INVENTION

Accordingly, an object of the present invention is to provide an automatic preparation apparatus and a support arm which allow the preparation process to be automatically performed while the support arm can be cleaned and yet in an interlocking relationship with a chromatography system.

According to the present invention, the object can be achieved by means of an automatic preparation apparatus comprising turntable means in which a plurality of test tubes can be disposed in the radial direction thereof, filter robot means which can move a removable filter onto one of the test tubes, probe robot means which can sample a predetermined amount of liquid contained in the test tubes and which can inject a predetermined amount of liquid into the tubes and filters, and control means for controlling the above-described means in accordance with a predetermined sequence to perform a desired preparation. The filter robot means has a support arm member for supporting the filter. The support arm member includes a head section having a filter retainer mechanism for releasably retaining the filter and a sealing mechanism for forming a sealing chamber on a sample-injecting side of the filter, an arm section having an end tip portion connected to the head section and a rear end portion attached to a support post member, and a device for detachably connecting the head section to the arm section.

Consequently, since the preparation can automatically be carried out without the intervention of manpower, treatment error and the contamination of samples can be prevented while treating time can be reduced to a great extent. Moreover, since it can automatically be run interlocking with the liquid chromatography system, component analysis and control of the preparation are extremely facilitated while highly reliable component analysis can automatically be achieved. Furthermore, since the head section is detachably connected to the arm section so that the entire head section can be detached and cleaned, the liquid attached to the support arm member can be completely removed therefrom. Accordingly, there is no case in which the liquid attached to the support arm member is mixed with a new liquid at the next filtering processing time and is solidified and the filter retainer mechanism for releasably retaining the filter, and the sealing mechanism for forming the sealing chamber on the sample-injecting side of the filter are unoperated, etc. Further, a head section mounting the filter of a different kind thereto can be also attached to the arm member.

The above-described turntable means is preferably provided with a turntable in which a plurality of test tubes can be arranged in radial directions, and drive means which allows the turntable to be turned in a horizontal plane so that one of the test tubes can be moved to a position where it is to be treated.

The probe robot means preferably comprises a probe needle the tip of which can be inserted into the above-described test tube and filter, a microsyringe pump which can suck and discharge a predetermined amount of liquid via the probe needle, horizontal drive means for horizontally driving the probe needle, and vertical drive means for vertically driving the probe needle. The support post member is preferably provided with drive means which allows the arm member to be turned in a horizontal plane so that the exit end of the filter can be located immediately over one of the test tubes positioned at the positioned where the sample is treated.

Preferably, the support arm member is provided with means for feeding the pressurized gas into the sealing chamber.

It is preferable that a filter supply unit for supplying new filters and a discard box into which used filters are discarded are further provided while the drive means of the support post member is so arranged that it may turn the arm member so that the filter retainer means may be positioned immediately above the filter supply unit and the discard box.

Also, the support arm member preferably bears on the post member in such a way that it may turn in a vertical plane, or is provided with drive means which can turn itself by a predetermined angle in the vertical plane. Preferably, cleaning means is provided at a fixed position for cleaning the probe needle and the microcyringe pump while the tip of the probe needle may be inserted into the cleaning means. Also, an input port for the chromatography system is preferably provided at a fixed position while the tip of the probe needle is so arranged that it may be inserted into the input port.

The control means is preferably provided with a microcomputer in which a sequence for carrying out the desired pretreatment is programmed, and the drive of the turntable means, filter robot means and the probe robot means may be controlled in accordance with the instructions from the microcomputer.

The filter preferably has an inner diameter of the port of above 6 mm for sample injection.

Furthermore, the ratio of the inner diameter of the sample injection port to that of the exit port preferably ranges 3:1 to 10:1.

Further objects and advantages of the present invention will be apparent from the following description of the preferred embodiment of the invention as illustrated in the accompanying drawings.

DESCRIPTION OF THE PREFERRED EMBODIMENTS

Figure 1:
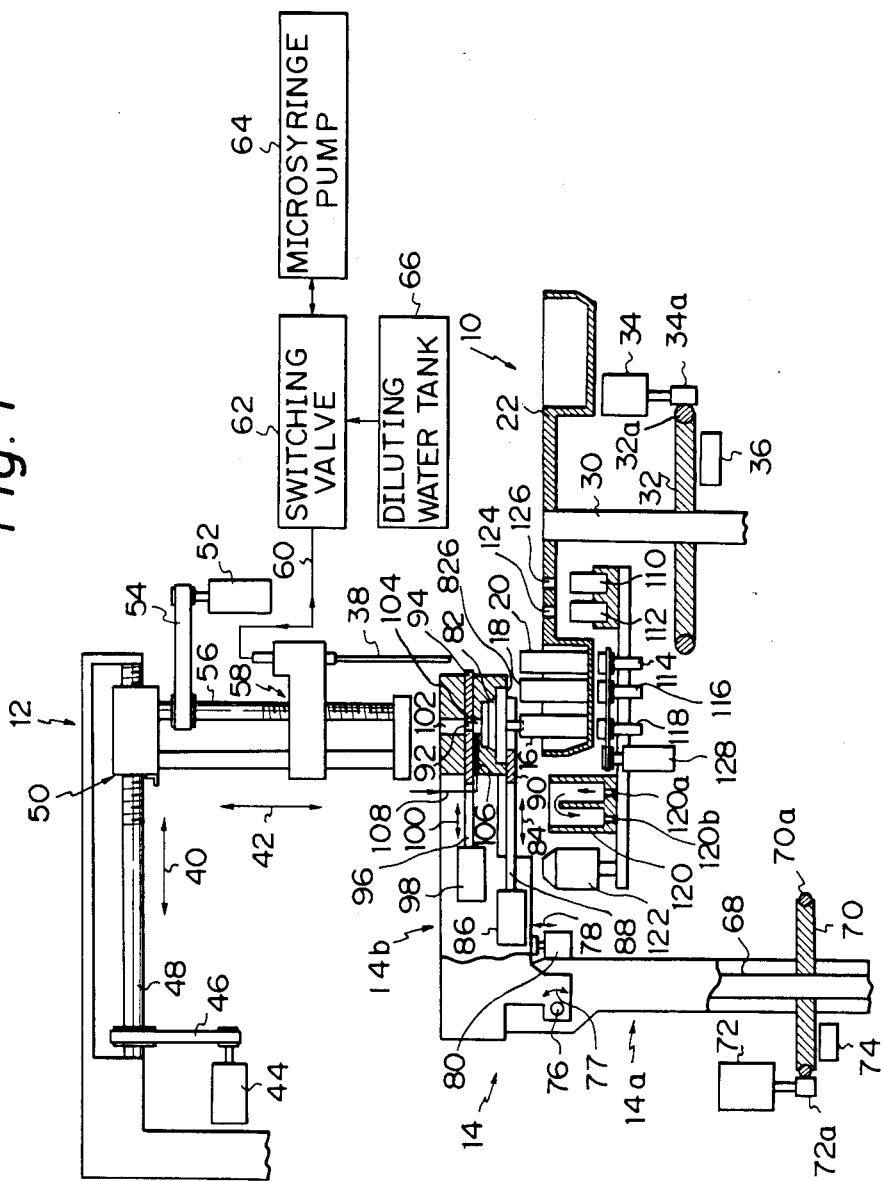
FIG. 1 is a schematic representation of one embodiment according to the present invention.

FIG. 1 schematically shows an arrangement of one embodiment according to the present invention. This embodiment refers to a case where the automatical preparation apparatus made in accordance with the present invention interlocks with the liquid chromatography system.

Figure 2:
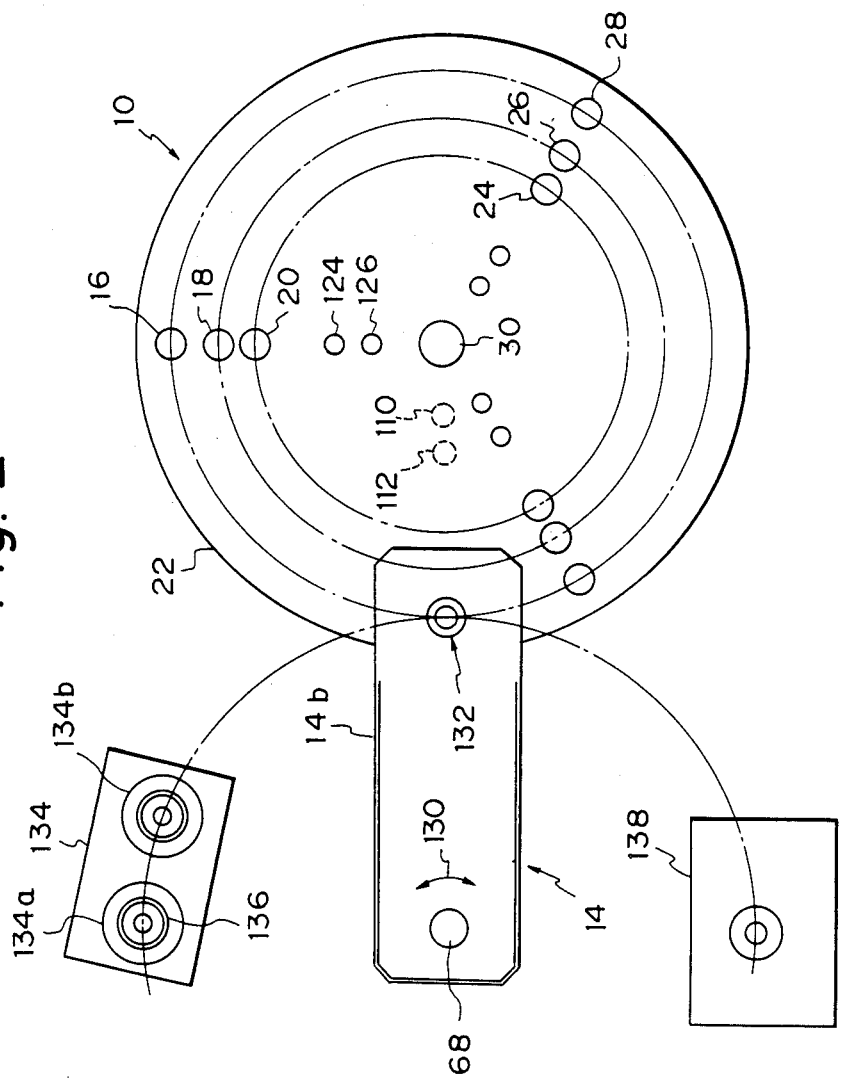
FIG. 2 is a partial plan view of the embodiment of FIG. 1.

FIG. 2 is a plan view presented for better understanding the arrangement and operation of the above-mentioned embodiment.

Generally, the apparatus according to the invention comprises turntable means 10, probe robot means 12, filter robot means 14, and control means (not shown in FIG. 1) for controlling these means. The turntable means 10 has a turntable 22 which allows a plurality of test tubes 16, 18 and 20 to be sequentially laid in the radial direction. The test tubes 16, 18 and 20 constitutes a group of test tubes for a single cycle of preparation. A further group of test tubes, for example, 24, 26 and 28 (FIG. 2) may be laid on the turntable 22 in another radial direction. The number of the group of test tubes which is to be laid on the turntable is not always restricted to three as illustrated in FIG. 2, and for example, 4, 8, 12, 20, 24, 32, 36, 40 or other number may also be conceived. Also, the number of test tubes which can be laid in one radial direction (i.e. a single group of test tubes) is three in this embodiment, but any number greater than one may be used.

The turntable 22 is fixed to a rotating shaft 30 and is turned in a horizontal plane together with the rotation shaft 30. The rotation shaft 30 is driven by rotating a drive disc 32 provided therebelow by means of an electric motor 34.

In this embodiment, a rubber ring 32a provided along the outer periphery of the disc 32 is rotated by a roller 34a of the motor 34. A gear drive or belt drive may also be used other than a combination of the rubber ring and roller. When usual AC or DC motor is used for the electric motor 34, position marks previously provided on a surface of the drive disc 32 may be detected by an optical sensor 36 for feedback control of the position of the turntable 22. In this case, if stepping motor is used as electric motor, this sensor may be omitted.

The probe robot means 12 is provided with a probe needle 38 which may sample and inject the sample liquid, diluting water or the like contained in the test tube by a predetermined amount, and drive means which may horizontally (left to right) and vertically (arrow 42) move the probe needle 38 as seen from FIG. 1. The horizontal drive of the needle 38 may be effected by transforming the rotational movement of a rotation shaft 48 into a horizontal displacement by a worm gear 50. The rotation shaft 48 may be rotated via a belt 46 by means of an electric motor 44. The vertical drive of the needle 38 may be effected by transforming the rotational movement of a rotation shaft 56 into a vertical displacement by the worm gear 58. The rotation shaft 56 may be rotated via a belt 54 by an electric motor 52. In this embodiment, the electric motors 44 and 52 are constituted by stepping motors.

To the probe needle 38 is connected a microcyringe pump 64 (diluter) via a passage 60 and a switching valve 62. The microsyringe pump 64 may be of known type, and sucks and discharges a predetermined amount of liquid. A diluting water tank 66 is further coupled to the switching valve 62.

The filter robot means 14 comprises a vertically extending support post member 14a and an arm member 14b which extends horizontally from the top of the support post member 14a. The support post member 14a has a rotation shaft 68 of which rotation may cause the support post member 14a and the arm member 14b to rotate. The rotation shaft 68 may be driven by rotating a drive disc 70 provided thereabove by means of an electric motor 72. In this embodiment, a rubber ring 70a which is provided along the outer periphery of the drive disc 70 is rotated by a roller 72a of the electric motor 72. A gear drive or a belt and pulley may be used for the combination other than the roller. When usual AC or DC motor is used as the electric motor 72, the position marks previously provided on a surface of the disc drive 70 may be detected by an optical sensor 74 for feedback control of the position of the rotating filter robot means 14. If stepping motor is used as the electric motor 72, a sensor 74 may be omitted.

The arm member 14b is so arranged that it cannot only be turned about the rotation shaft 68 (in the direction of the arrow 130 indicated in FIG. 2) in the horizontal plane, but also be turned by a predetermine angle in the direction indicated by the arrow 77, around a support shaft 76 as its axis, so that its tip portion may vertically be moved.

Thus, during filtering process, the exit end of the filter to be described later can be inserted into the interior of the test tube with the result that part of the filtered liquid will not flow out of the test tube. This rotation of the arm member 14b may be achieved by a torque applied by a pneumatic cylinder 80, which carries out a reciprocating movement as indicated by an arrow 78 by the compressed air, to the arm member 14b.

At the tip portion of the arm member 14b is provided with a filter retainer mechanism for releasably retaining a disposable molded filter, a sealing mechanism for defining a sealing chamber at the side of the filter 82 where the sample may be injected, and a mechanism for feeding the compressed air into this sealing chamber. In this embodiment, the disposable filter 82 has an open-type thermoplastic housing having a larger diameter at the sample injecting side than that of the exit side. The details of this disposable filter 82 will be hereinafter described.

Figure 3:
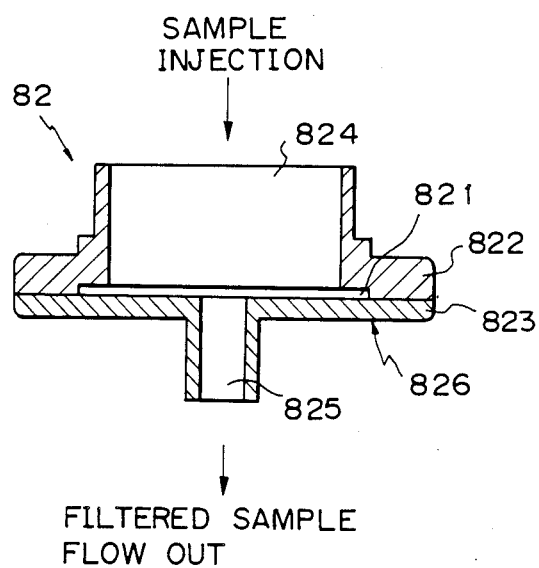
FIG. 3 is a cross sectional view illustrating a filter according to the present invention used in the apparatus shown in FIG. 1.

FIG. 3 illustrates a cross section of such a disposable filter. A filter medium 821 is integrally formed interleave with the thermoplastic housings 822 and 823. The inner diameter of the sample injection port 824 is above 6 mm, preferably above 10 mm, and more preferably above 20 mm.

The exit 825 of the filtrate is usually 3 to 5 mm. The ratio of the inner diameter of the injection port 824 to that of the exit 825 is 3:1 to 10:1, preferably 5:1 to 10:1, and more preferably 6:1 to 10:1.

The material of the filter medium 821 is not specifically restricted. For example, filter paper, membrane filter, glass filter, charcoal filter, or ion exchange membrane may be used as used for the conventional disposable molded filter. Besides, not only a single filter but also one or more prefilters may be integrally formed thereon in a closely overlapping relationship depending on the properties of the sample to be filtered.

The materials of the prefilters are not specifically restricted, but any filter which has been used to the conventional molded filters may of course be used as such. Furthermore, for ease of the outflow of the filtrate and the increase of filtration speed, the thermoplastic, metallic, ceramic, or glass support provided with recesses or grooves may integrally and closely be overlapped with the filter. Otherwise, it is preferable that the recesses or grooves are formed at the portion of the housing facing the surface of the filter to ease the outflow of the filtrate.

Thermoplastics such as polypropylene, or polystylene are preferably used as the material for the housings 822 and 823. The disposable filter 82 according to the present invention can be made by the same method as in the conventional disposable filter and requires no special method.

As to its shape also, it is not specifically restricted to any special one aside from the size of the injection port, and may be the same as in the conventional disposable filter.

Figure 4:
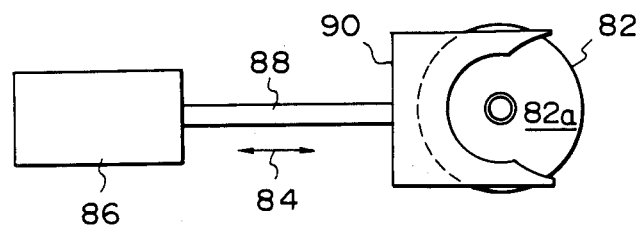
FIG. 4 is a bottom view of filter retainer means according to the embodiment of FIG. 1.

The filter retainer mechanism is so arranged that it may retain the filter 82 from below by abutting against part of lower surface 826 of the filter. FIG. 4 is a bottom view illustrating the retainer mechanism in a retaining state. That is, a retainer member 90, which is coupled via a rod 88 to a pneumatic cylinder 86 reciprocating in the direction indicated by the arrow 84 by the compressed air, supports part of the lower surface 826 of the filter 82. When the filter 82 is discarded, the retainer member 90 is moved in the leftward direction and the filter 82 will drop by its own weight.

The sealing mechanism comprises a shutter member 94 which has a through hole 92 and which may sealingly slide in the horizontal direction, and a pneumatic cylinder 98 coupled to the shutter member 94 via a rod 96. When the pneumatic cylinder 98 drives the rod 96 by the compressed air in the horizontal direction (indicated by the arrow 100), the shutter member 94 may open or close the injection port 102 to thereby form the sealing chamber 104 at the lower side thereof. The compressed air or gas such as nitrogen can be applied to the sealing chamber 104 from a compressed gas source (not shown) via a hole 106 and a passage 108. Application of the compressed gas into the sealing chamber 104 may cause the injected sample to be filtered under pressure.

The rotation shaft 30 of the turntable means 10, rotation shafts 48 and 56 of the probe robot means 12, and the rotation shaft 68 of the filter robot means 14 all lie in the same plane as shown in FIG. 1 with respect to their axial lines.

Reagent tubes 110 and 112, agitators 114, 116 and 118, cleaning mechanism 120, and an automatic six-way switching valve 122 which may serves as an input port for the liquid chromatography system, are successively fixed at predetermined positions between the rotation shafts 30 and 68, so that each center of them may lie in the above-mentioned plane.

The reagent tubes 110 and 112 are intended for previously containing reagents used during the reactive treatment mode, and through holes 126 and 124 are provided in each radial direction at corresponding portions of the turntable 22 in such a way that the probe needle 38 may be inserted into those reagent tubes 110 and 112.

Agitators 114, 116 and 118, which are of known magnet-driven type for agitating samples, are so disposed that when the test tubes lie in the above-described plane (see positions of the test tubes 20, 18 and 16 of FIG. 1) they may be located just below those test tubes.

S- and N-poles are respectively positioned at the radial ends of the upper portions of those agitators and are rotated by means of the electric motor 128 to agitate the magnetic particles (stirrer) contained within the test tubes.

The cleaning mechanism 120 is intended for cleaning the probe needle 38 and elements communicating therewith, and at least during the operation, cleaning liquid flows as indicated by the arrow via openings 120a and 120b, which communicate with a cleaning liquid supply and discharge system (not shown).

The initial position of the probe needle 38 is set immediately above this cleaning mechanism 120. The automatic six-way switching valve 122 is a known input port for injecting the sample into the chromatography system.

The arm member 14b of the filter robot means 14 can be turned in the direction indicated by the arrow 130 of FIG. 2 but in this embodiment it may stop at four positions, one of which is the one indicated in FIG. 2 where it stops while the sample is being filtered. In this case, the exit end of the disposable filter is positioned in alignment with the position 132 of a test tube, i.e. the test tube 16 of FIG. 1, disposed at the outermost side of the treatment position.

Besides, it can stop respectively at two filter supply positions 134a and 134b of the filter supply unit 134 of FIG. 2.

The filter supply unit 134 forces up one of the new disposable filters, for example a disposable filter 136, from either one of the two filter supply portions 134a and 134b to fit it with a predetermined portion on the lower surface of the arm member 14b, i.e., the filter retainer mechanism. The disposable filter may be retained by the retainer member 90, as described above. The arm member 14a further stops at a discard box 138 (FIG. 2) for discarding the used filters.

Figure 5:
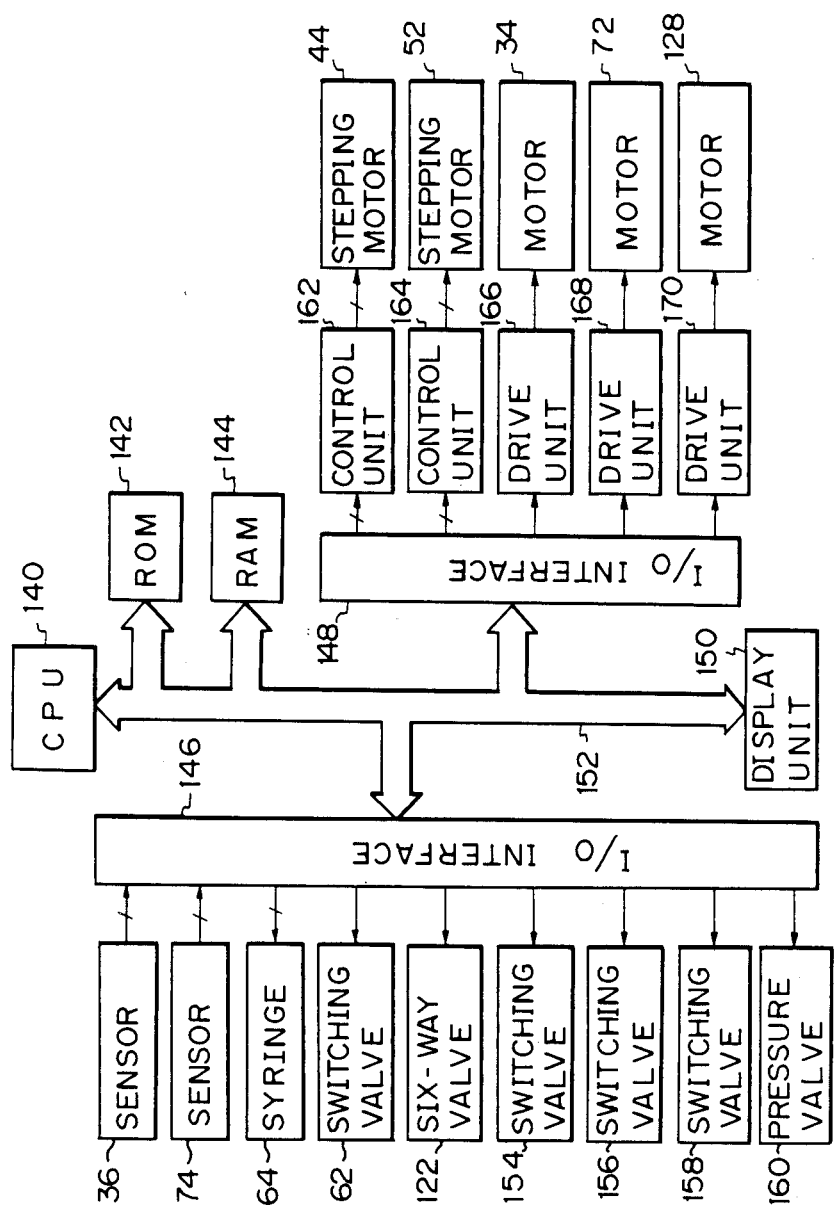
FIG. 5 is a block diagram of control means.

FIG. 5 is a block diagram schematically illustrating the electrical constitution of the control means used in this embodiment. As seen from the figure, in this embodiment, a microcomputer is used which comprises a central processing unit (CPU) 140, read only memory (RAM) 144, input/output (I/O) interfaces 146 and 148, display unit and buses for connecting those.

The sensors 36 and 74 are connected to the I/O interface 146 and the detected position data signals are input into the microcomputer. To the I/O interface 146 are further connected the microsyringe pump 64, the switching valve 62, and the automatic six-way switching valve 122 in order to be controlled by the signals issued from the microcomputer.

Furthermore, to the I/O interface 146 are connected compressed air switching valves 154, 156 and 158 for controlling the reciprocating movement of the pneumatic cylinders 80, 86 and 98, respectively. Thus the microcomputer controls these pneumatic cylinders. A pressure valve 160 is further connected to the I/O interface 146 for switchingly controlling the application of the compressed air into the sealing chamber 104. This pressure valve 160 is disposed on the way of the passage 108 of FIG. 1.

Control units 162 and 164 are connected to the I/O interface 148 for controlling the rotation of the stepping motor 44 and 52. Thus the position of the probe needle 38 is controlled by the microcomputer. Further, drive units 166 and 168 are connected to the I/O interface 148 for driving the electric motors 34 and 72, and thus the positions of the turntable 22 and the filter robot means 14 are be controlled by the microcomputer in accordance with the signals issued from the sensors 36 and 74. Finally, a drive unit is connected to the I/O interface 148 to drive the electric motor 128 for driving the agitators 114, 116 and 118. Thus, on-off of the electric motor 128 is controlled by the microcomputer.

Figure 6:
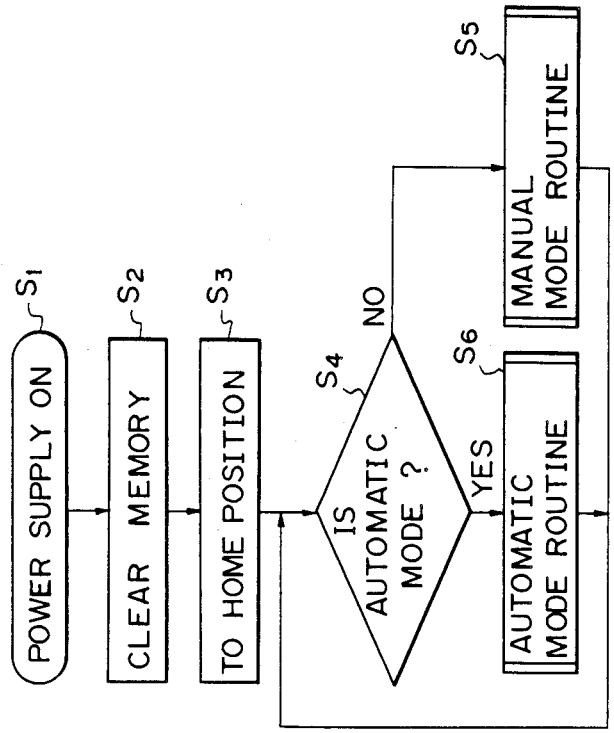
FIGS. 6 and 7 are respectively a flow chart of a program incorporated in the microcomputer of the control means.
Figure 7:
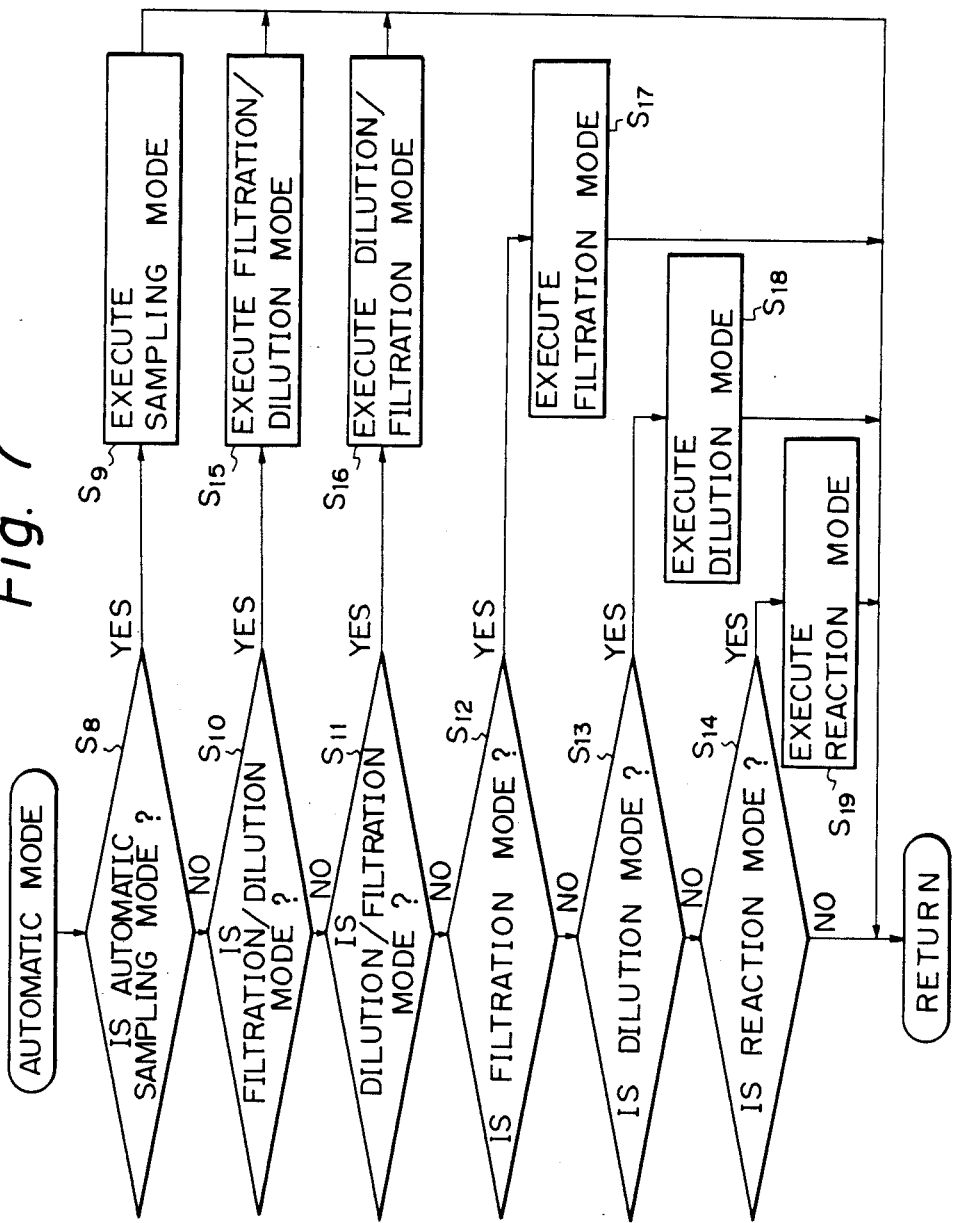

The principle of operation of the embodiment is hereinafter described with specific reference to the accompanying drawings in which;

FIGS. 6 and 7 are respectively a flow chart schematically illustrating one example of the control program stored within the microcomputer. When power supply is turned on (step $S_1$ of FIG. 6), the CPU 140 clears the RAM 144 and other memories (step $S_2$), and then resets all the drive elements to their home positions (original positions (step $S_3$). This means that, with respect to the turntable means 10, the group of test tubes to be started is to be restored to the treating position; with respect to the probe robot means 12, the probe needle 38 is to be positioned to a predetermined height immediately above the cleaning mechanism 120; and with respect to the filter robot means 14, the arm member 14b is to be previously turned up to the position of the filter supply unit 134. Then it is judged whether the further operations should be carried out automatically or manually (step $S_4$), and if it is judged to be manually carried out, the program will proceed to a manual mode routine (step $S_5$) for manual preparation. Since the detail of each preparation by the manual mode routine is substantially the same as those of the automatic mode routine, further explanation of it is omitted.

If the automatic operation is judged, the program will proceed to the automatic mode routine (step $S_6$).

The detail of the automatic mode routine is shown in FIG. 7. In this routine, the microcomputer first judges whether automatic sampling mode is set or not (step $S_8$). If yes, the program proceeds to execute a sampling mode (step $S_9$). This sampling mode will be later described in more detail. If not, the microcomputer sequentially judges whether a filtration/dilution mode (step $S_{10}$), dilution/filtration mode (step $S_{11}$), filtration mode (step $S_{12}$), dilution mode (step $S_{13}$), or reaction mode (step $S_{14}$) has been set or not. If any one of these mode has been determined to be set, that mode will be executed (step $S_{15}$, $S_{16}$, $S_{17}$, $S_{18}$ or $S_{19}$).

The operations of the above-described modes are hereinafter described.

(A) Filtration/Dilution Mode

The sample liquid to be treated is previously contained within the test tube disposed on the second track counting from the outermost track (corresponding to the test tube 18 in FIG. 1). The test tubes disposed along this track are hereinafter referred to as sample tubes. Further, the test tubes disposed along the outer most and innermost tracks are referred to as filtrate tubes (corresponding to the test tube 16) and dilution tubes (corresponding to the test tube 20) respectively.

Figure 8:
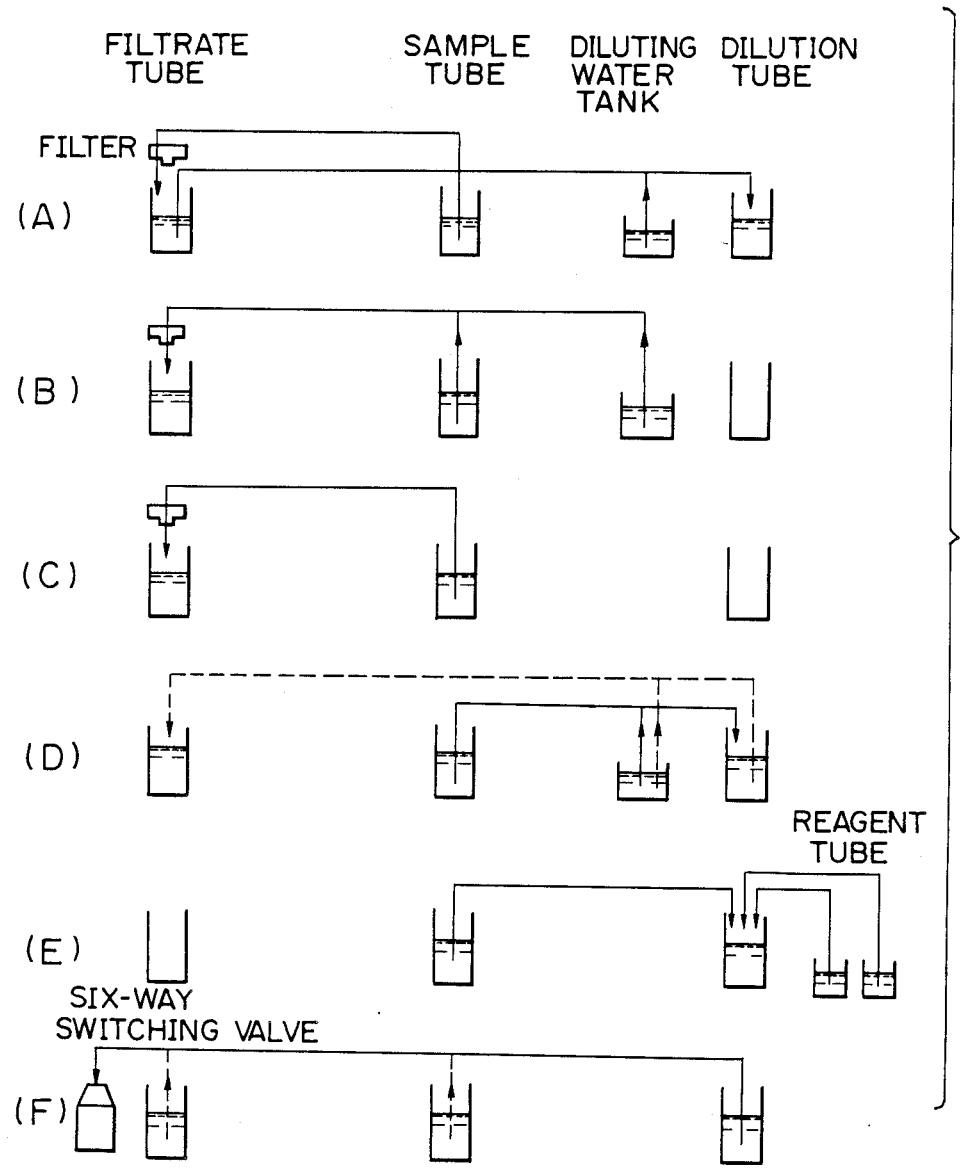
FIG. 8 is an explanatory view of each operation mode.

As shown in (A) of FIG. 8, this filtration/dilution mode refers to the operation mode in which after the sample liquid in the sample tube has been filtered by the disposable filter, the resultant filtrate is poured into the dilution tube together with the diluting water. The operation sequence of this mode is hereinafter described.

(1) First, unused new disposable filter is fitted to a predetermined position of the arm member 14b by the filter supply unit 134.

(2) Next, the pneumatic cylinder 86 is actuated to move the retainer member 90 to fix and retain the disposable filter 82 as shown in FIG. 1.

(3) Then the stepping motor 44 is first driven to move the probe needle 38 until it stops immediately above the sample tube 18.

(4) The stepping motor 52 is driven to lower the probe needle 38 until it can sample the sample liquid.

(5) The microsyringe pump 64 is driven to sample the sample liquid.

(6) The stepping motor 52 is driven to raise the probe needle 38.

(7) The pneumatic cylinder 80 is actuated to make the tip portion of the arm member 14b face upwardly by a predetermined angle.

(8) The electric motor 72 is driven to turn the arm member 14b up to the position where the sample is to be treated. That is, the arm member 14b is turned to the position shown in FIG. 2.

(9) The pneumatic cylinder 80 is again actuated to restore the arm member 14b to its horizontal position. As a result the exit end of the disposable filter 82 may be inserted into the filtration tube 16 as shown in FIG. 1.

(10) The stepping motor 44 is driven to move the probe needle 38 immediately above the disposable filter 82.

(11) The stepping motor 52 is driven to insert the probe needle 38 into the sample injection port 102.

(12) The microsyringe pump 64 is driven to inject the sampled liquid into the sealing chamber 104.

(13) The stepping motors 44 and 52 are driven to restore the probe needle 38 to its initial position.

(14) The pneumatic cylinder 98 is actuated to move the shutter member 94 rightwardly (FIG. 1) with the result that the sealing chamber 104 is sealed.

(15) The pressure valve 160 is turned on and the compressed air is applied into the sealing chamber 104. Consequently, the sample liquid contained within the sealing chamber 104 is pressurized and filtered by the disposable filter 82 to flow down to the filtrate tube 16.

(16) The pressure valve 160 is turned on.

(17) The pneumatic cylinder 98 is actuated to move the shutter member 94 back to its initial position.

(18) The pneumatic cylinder 80 is actuated to make the arm member 14b face upwardly.

(19) The electric motor 72 is driven to turn the arm member 14b up to its initial position.

(20) The stepping motor 52 is driven and the probe needle 38 is lowered to be inserted into the cleaning mechanism 120. After the probe needle and the elements communicating therewith have been cleaned therein, the probe needle 38 is raised up to its initial position.

(21) The electric motor 34 is driven to turn the turntable 22 until the next group of test tubes to be treated reaches the treating position.

(22) The sequence from step (3) to step (21) is repeated and the number of treating cycles (number of groups of test tubes) is completed.

(23) The electric motor 72 is driven to turn the arm member 14b until the disposable filter 82 reaches immediately above the discard box 138.

(24) The pneumatic cylinder 86 is actuated to move the retainer member 90 leftwardly (FIG. 1). As a result, the disposable filter 82 is discarded and then the arm member 14b is restored to its initial position.

(25) The electric motor 34 is driven to turn the turntable 22 until it restores to its starting position. That is, a group of test tubes to be started comes along again to the treating position.

(26) The stepping motor 44 is driven to move the probe needle 38 immediately above the filtrate tube 16.

(27) The stepping motor 52 is driven to lower the probe needle 38 to a position where it can sample the filtrate contained within the filtrate tube 16.

(28) The microsyringe pump 64 is driven to sample the filtrate.

(29) The stepping motor 52 is driven to raise the probe needle 38.

(30) The stepping motor 44 is driven to move the probe needle horizontally until it reaches immediately above the dilution tube 20.

(31) The stepping motor 52 is driven to insert the tip of the probe needle 38 into the dilution tube 20.

(32) The microsyringe pump 64 is driven to inject the filtrate sampled in step (28) into the dilution tube 20.

(33) The switching valve 62 is actuated to make the diluting water tank 66 communicate with the microsyringe pump 64.

(34) The microsyringe pump 64 samples a proper amount of diluting water from the tank 66.

(35) The switching valve 62 is switched to its original position.

(36) The microsyringe pump 64 is actuated to inject the diluting water into the dilution tube 20 to thereby prepare the diluting liquid of a predetermined concentration.

(37) The stepping motor 52 is driven to raise the probe needle 38.

(38) The stepping motors 44 and 52 are driven to move the probe needle 38 horizontally and downwardly for cleaning. Then the probe needle 38 is again raised up to its initial position.

(39) The electric motor 34 is driven to turn the turntable 22 until the next group of test tubes comes to the treating position.

(40) The sequence from step (26) to (39) is repeated and the number of the treating cycles is completed.

(B) Dilution/Filtration Mode

As shown in (B) of FIG. 8, this mode refers to the operation mode in which the sample liquid within the sample tube and the diluting water are filtered together by means of the disposable filter. In executing this mode, subsequent to the above-described step (12), a step is added in which a predetermined amount of diluting water fed from the diluting water tank 66 is injected into the sealing chamber 104, and following steps are followed up to step (24) or, after steps (33) to (35) have been executed, steps (3) to (24) may be followed.

(C) Filtration Mode

As shown in (C) of FIG. 8, this mode is intended for filtering the sample liquid contained within the test tube by the disposable filter in accordance with steps (1) to (24) only.

(D) Dilution Mode

This mode may comprise a primary and secondary dilution modes. The former, as indicated by the solid line drawn in (D) of FIG. 8, injects the sample liquid within the sample tube and the diluting water into the dilution tube, and the latter, as indicated by the broken line drawn in (D) of FIG. 8, injects the sample liquid within the dilution tube, which was diluted as described above and the diluting water, into the filtrate tube.

The operation sequence in those two modes is similar that of steps (26) to (40). That is, the primary dilution mode only differs from that in that the sample liquid within the sample tube is sampled in place of the sample liquid within the filtrate tube while the secondary dilution mode only differs from that in that the primary diluting liquid within the dilution tube is sampled in place of the filtrate within the filtrate tube to inject the secondary diluting liquid. Therefore, further explanation of the detail of that operation sequence is omitted.

(E) Reaction Mode

As shown in (E) of FIG. 8, this mode relates to mixing the sample liquid within the sample tube with the reagent I and/or II within the reagent tubes for reaction If they should be agitated for better mixing effect, magnetic particles (stirrers) are previously accommodated therein.

The operation sequence of this mode is hereinafter described.

(51) The above-described steps (3) to (6) are followed.

(52) The stepping motor 44 is driven to move the probe needle 38 until it reaches immediately above the dilution tube.

(53) The stepping motor 52 is driven to insert the probe needle 38 into the dilution tube.

(54) The microsyringe pump 64 is driven to inject the sample liquid into the dilution tube.

(55) The stepping motors 44 and 52 are driven to raise, horizontally move and lower the probe needle 38 for cleaning by means of the cleaning mechanism 120. Then the probe needle 38 is again raised and horizontally moved until it is located immediately above the reagent tube 112.

(56) The probe needle 38 is lowered by means of the stepping motor 52 so that the reagent I contained within the reagent tube 112 may be sampled.

(57) The microsyringe pump 64 is driven to sample the reagent I.

(58) The stepping motors 44 and 52 are driven to raise, horizontally move and lower the probe needle 38 for insertion into the dilution tube.

(59) The microsyringe pump 64 is driven to inject the reagent I into the dilution tube.

(60) The reagent II is injected into the dilution tube by the similar operation as in the steps (55) to (59).

(61) After the probe needle 38 has been cleaned, it is restored to its initial position by means of the stepping motors 44 and 52.

(62) The electric motor 128 is driven to rotate the agitator 114 for agitation.

(63) After agitation, as the occasion demands, the sampling mode (described later) is immediately followed to inject the reaction liquid within the dilution tube into the automatic six-way switching valve 122.

(64) The electric motor 34 is driven to turn the turntable 22 until the next group of test tubes reaches the treating position.

(65) The above-described sequence is repeated to complete the specified number of cycles.

In the above-described sequence, the sample liquid within the sample tube is transferred into the dilution tube for reaction, but the reagent may directly be injected for reaction into the sample tube. Besides, it is also possible that the reagent is previously contained within the filtrate tube and, further, the dilution tube (in the above-described case). Furthermore, two reaction tubes may also be used. In this case, reaction treatment may be carried out with the capacity which may be large as more than twice as otherwise.

(F) Automatic Sampling Mode

This mode, as shown in (F) of FIG. 8, may inject the pretreated liquid within the filtration tube, sample tube or dilution tube into the automatic six-way switching valve 122 of the chromatography system.

In this embodiment, this mode is to be executed after all the groups of test tubes have been prepared, but may be executed after the completion of each cycle, i.e., each time a single cycle is ended. In the latter case, the number of test tubes may be 32 sets so that the preparation and the component analysis may automatically be carried out for 12 hours in a row, and if the number is set to 64, this mode can automatically be run for 24 hours in a row.

The operation sequence of this mode is hereinafter described. Yet the above-described sequence relates to a case where the liquid within the dilution tube is sampled.

(70) First, the stepping motors 44 and 52 are driven to horizontally move and lower the probe needle 38 down to a position where the liquid within the dilution tube maybe sampled.

(71) The microsyringe pump 64 is driven for suction.

(72) The stepping motors 44 and 52 are driven to raise, horizontally move and lower the probe needle 38 for insertion into the injection port of the six-way switching valve 122.

(73) The six-way switching valve 122 is switched.

(74) The microsyringe pump 64 is driven for injection.

(75) The probe needle 38 is raised.

(76) The six-way switching valve 122 is switched to its original position.

(77) The probe needle 38 is cleaned and is restored to its initial position.

Aside from the above-described operation modes, filtration mode and dilution mode may respectively be executed any number of time for a single group of test tubes. But in this case, the number of test tubes for each group will be the one obtained by adding 1 to the number of operation modes to be executed. That is, when the filtration mode and the dilution mode are respectively set to a single time, three ($=2+1$) test tubes will be required for each group, and when the former and the latter are respectively set to 1 and 2 times, four (=3+1) test tubes will in all be required for each group.

According to the above-described embodiment, the filter robot means 14 cannot be horizontally moved in the central direction of the turntable 122, but if such a horizontal movement is allowed, the position of the filtrate tube can be altered to the other track than the outermost track. For example, it will be possible to effect the filtration and dilution by disposing tubes in the order of dilution tube/sample tube/filtrate tube, sample tube/dilution tube/filtrate tube, sample tube/filtrate tube/dilution tube, or dilution tube/filtrate tube/sample tube respectively, the filtration can successfully be done for double capacity of the sample by disposing them in the order of filtrate tube/sample tube/filtrate tube.

Figure 9:
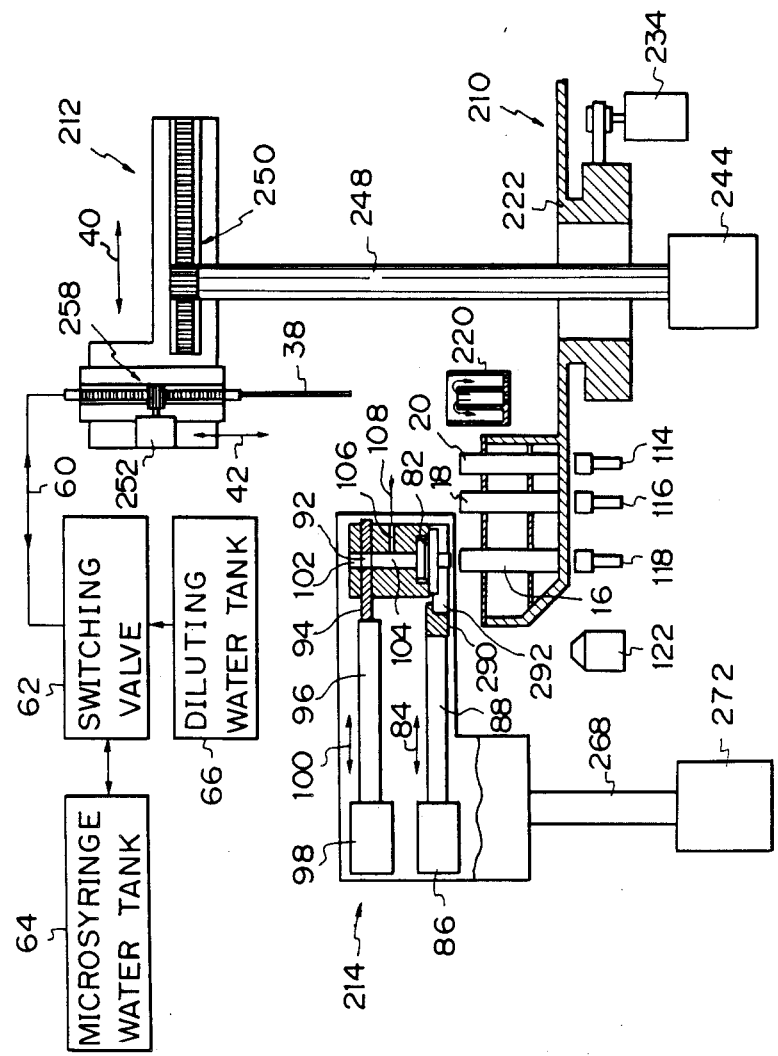
FIG. 9 is a view schematically illustrating the arrangement of another apparatus embodying the present invention.

FIG. 9 schematically illustrates the arrangement of another embodiment according to the present invention. The arrangement of this embodiment is basically the same as that of FIG. 1, and only the differences are hereinafter described. Like elements of the same construction and function as the ones in FIG. 1 are designated by the same numerals.

First, as to the turntable means 210, shape of a turntable 222 is slightly different and it is belt-driven by an electric motor 234. However, function of this turntable means is essentially the same as that of FIG. 1. As to the cleaning mechanism 220, its position and construction are different.

As to the probe robot means 212, the probe needle 38 is horizontally driven via a rack and pinion gear 250 from a rotation shaft 248 directly driven by an electric motor 244 while vertically driven via the rack and pinion gear 258 from an electric motor 252, but its function is the same as the embodiment of FIG. 1.

Figure 10:
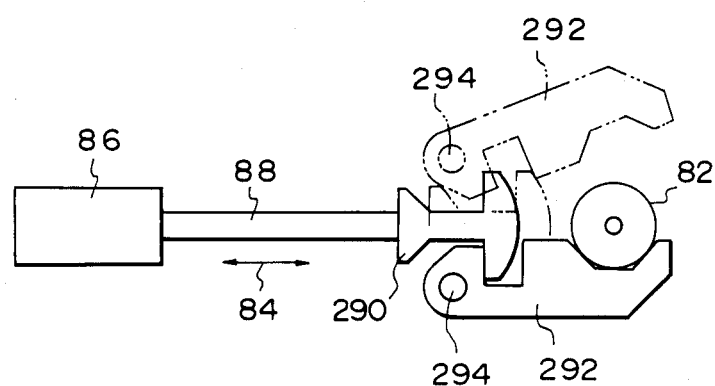
FIG. 10 is a bottom view of the filter retainer means according to the embodiment of FIG. 9.

In the filter robot means 214, a rotation shaft 268 is directly driven by means of an electric motor 272, but the greatest difference lies in the fact that in this embodiment its arm member can only be turned in the horizontal plane and does not turn in the vertical plane as in the embodiment of FIG. 1, which makes the former simpler in construction. Furthermore, the retainer mechanism of the disposable filter 82 is different in construction from the embodiment of FIG. 1. FIG. 10 illustrates bottom view of the retainer mechanism. That is, when a pneumatic cylinder 86 causes a rod 88 to travel in the rightward direction as shown in the figure, a cam member 290 forces down a clamp member 292 with the result that the clamp member 292 is opened with the axis 294 as its center as shown by the two-dotted chain line. After the disposable filter is inserted between the two clamp members 292 in this state, if the pneumatic cylinder 86 is actuated to drive the rod 88 and hence the cam member 290 in the leftward direction, the clamp member 292 is closed as shown by the solid line to abut the outer periphery of the filter 82 for securement.

Since the operation of this embodiment is approximately the same as the one of the embodiment of FIG. 1, further explanation is omitted.

As described above, since the disposable filter having an open-type housing with a larger diameter at the injection side, the problem of contamination and the difficulty of positioning the injecting position can effectively be eliminated.

FIGS. 11 to 19 show a support arm of the filter in which an entire head section can be cleaned in accordance with the present invention. In these figures, the same or corresponding portions to those in FIGS. 1 to 10 are designated by the same reference numerals.

Figure 11:
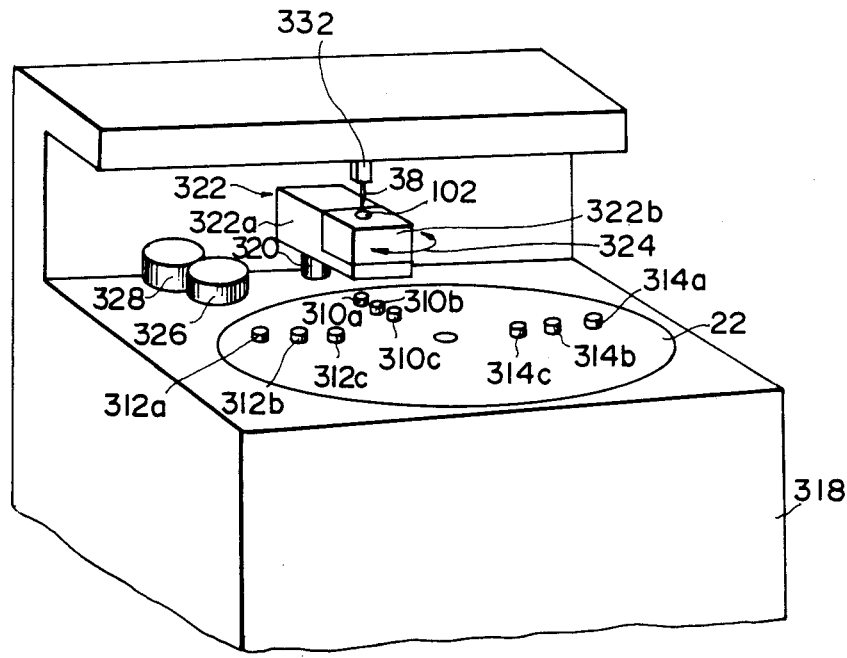
FIG. 11 is a perspective view schematically showing the entire preparation apparatus provided with a support arm of the filter in accordance with the present invention.

FIG. 11 schematically shows an entire preparation apparatus provided with a support arm of the filter in accordance with the present invention.

In the following embodiments shown in FIGS. 10 to 19, the filter means a disposal filter using a filter paper, a disposal ultra-filter using an ultrafiltering film, a disposal fixed phase container for extracting a solid phase using an enzyme or other filling material, an other container for separation, and a container combining these filters and the containers with each other.

A plurality of test tubes 310a, 310b, 310c (312a, 312b and 312c; or 314a, 314b and 314c) can be arranged on the turntable 22 in the radial direction thereof. This turntable 22 is disposed on an apparatus body 318 and can be rotated in accordance with the necessity such that the position of the turntable is movable. A rotatable support post member 320 is further disposed on the apparatus body 318, and a support arm member 322 of the filter is attached onto an upper portion of the support post member 320. Accordingly, the arm member 322 can be rotated with the rotary axis of the support post member 320 as a center as shown by an arrow 324 in FIG. 11. The arm member 322 is constructed by an arm section 322a and a head section 322b connected to an end tip thereof. The head section 322b can be located above the test tube 310a and filter supply positions 326 and 328.

An injection port 102 for injecting a sample is open on the upper side of the head section 322b and the probe needle 38 of the probe robot means 332 can be arranged above the injection port 102. The construction and function of the probe robot means 332 are the same as these of the aforementioned probe robot means.

Figure 12:
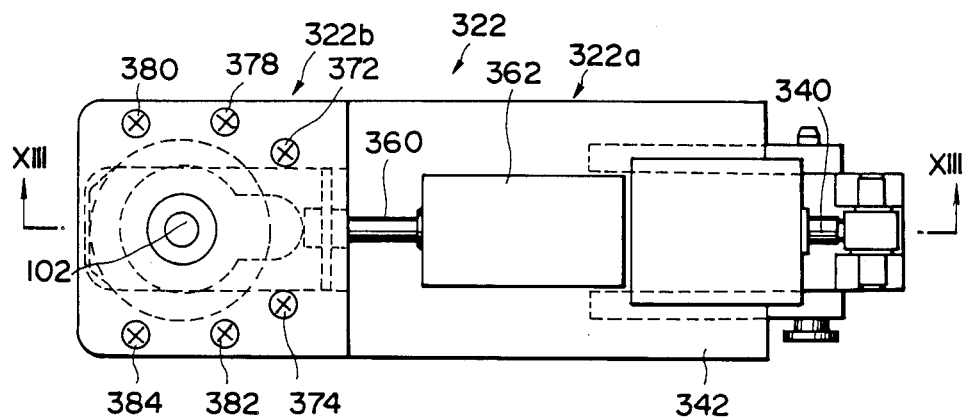
FIG. 12 is a plan view showing the construction of one embodiment of the support arm of FIG. 11.
Figure 13:
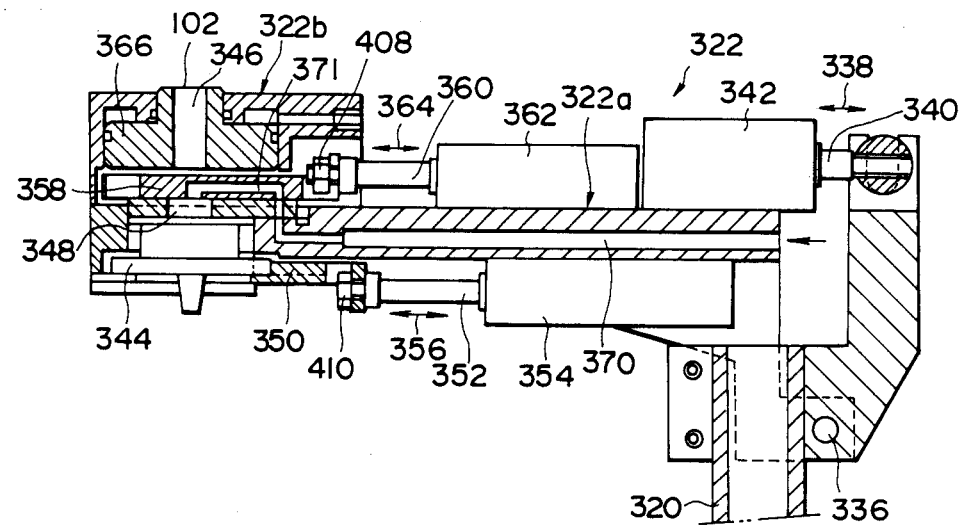
FIG. 13 is a cross-sectional view of the support arm taken along line XIII—XIII of FIG. 12.
Figure 14:
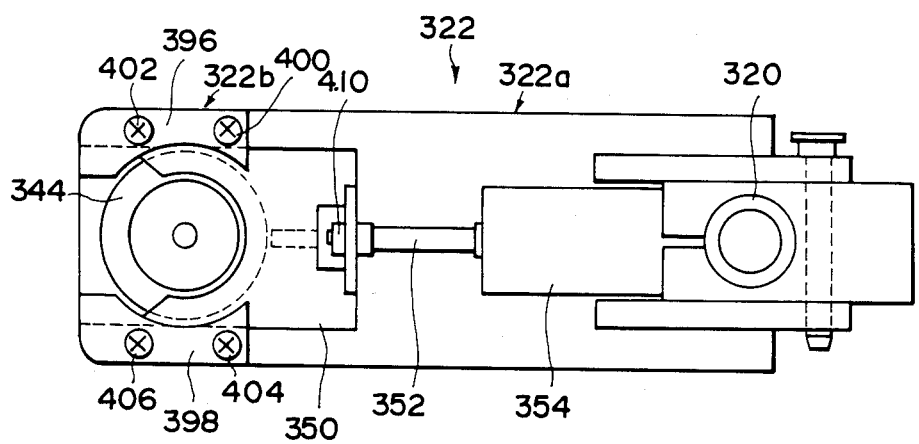
FIG. 14 is a bottom view of the support arm of FIG. 12.
Figure 15:
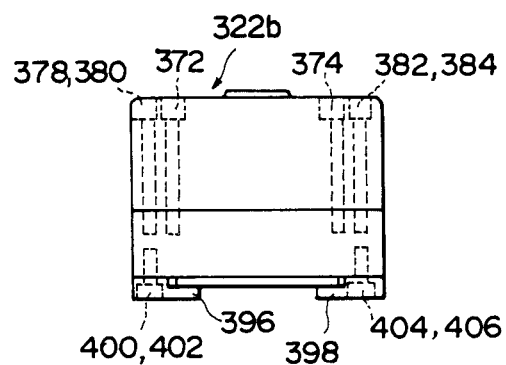
FIG. 15 is a side view of the support arm of FIG. 12.

FIGS. 12 to 15 show the construction of a preferred embodiment of the support arm member of FIG. 11. FIG. 12 is a plan view of the arm member, FIG. 13 is a cross-sectional view of the arm member taken along line XIII—XIII of FIG. 12, FIG. 14 is a bottom view of the support arm, and FIG. 15 is a side view of the arm member.

As mentioned before, the support arm member 322 is constructed by the arm section 322a and the head section 322b connected to an end tip thereof. A rear end portion of the arm section 322a is connected to the support post member 320 such that the arm section 322a can be rotated on a horizontal plane with the rotary axis of the support post member 320 as a center. The rear end portion of the arm section 322a is further constructed such that the arm section 322a is rotated by a predetermined angle on a vertical plane with a support shaft 336 as a center and therefore an end tip portion of the arm section 322a is vertically moved. This vertical movement is performed by a pneumatic cylinder 342 which is attached to the arm section 322a and has a rod 340 moved by the cylinder 342 forwards and backwards as shown by an arrow 338 of FIG. 13.

In this embodiment, the head section 322b has a filter retainer mechanism for releasably retaining a disposal filter 344 as a molded filter of a paper type, a through hole 346 communicated with the injection port 102, for injecting the sample to this disposal filter 344, a sealing mechanism for forming a sealing chamber 348 on the side of the through hole 346, and a passage for supplying the pressurized air to this sealing chamber 348.

The filter retainer mechanism is provided with a retainer member 350 for supporting a portion of the lower face of the disposal filter 344 fitted from below. This retainer member 350 is connected to a pneumatic cylinder 354 through a rod 352. The pneumatic cylinder 354 can move the rod 352 by the action of the pressurized air in the direction of arrow 356 in FIG. 13 so that retainer member 350 can hold or release the disposal filter 344.

The sealing mechanism is provided with a shutter member 358 which can interrupt the through hole 346 in an intermediate portion thereof to form the sealing chamber 348. This shutter member 358 is connected to a pneumatic cylinder 362 through a rod 360. The pneumatic cylinder 362 moves the rod 360 by the action of the pressurized air in the direction of an arrow 364 in FIG. 13 so that the above sealing operation can be performed by the shutter member 358. The sealing mechanism is further provided with a piston member 366 which can be hermetically slid in the vertical direction. This piston member 366 presses the shutter member 358 in the downward direction by the action of the pressurized air applied to this piston member through a passage so as to reliably improve the sealing performance of this shutter member 358. The through hole 346 mentioned above is disposed in the center of the piston member 366.

A passage 370 is communicated with a passage 371 disposed within the shutter member 358. Accordingly, when the shutter member 358 is closed, the pressurized air is supplied to the sealing chamber 348 through these passages 370 and 371.

Figure 16:
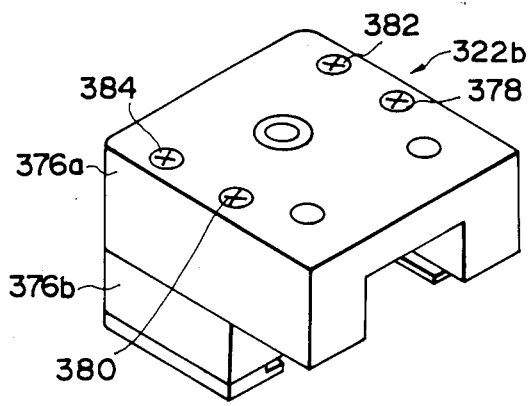
FIG. 16 is a perspective view of a head section detached from the support arm of FIG. 12.

In this embodiment, the head section 322b is detachably connected to the arm section 322a. Namely, in this embodiment, as shown in FIGS. 12 and 15, the head section 322b except for the retainer member 350 and the shutter member 358 is fixed to the arm section 322a by bolts 372 and 374 and can be easily detached from the support arm member 322 by unfastening and detaching these bolts 372 and 374. FIG. 16 shows the head section 322b detached from the support arm member 322 in this way.

Figure 17:
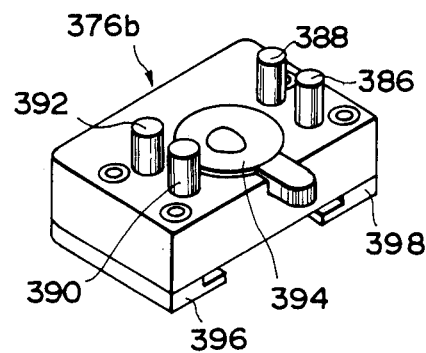
FIG. 17 is a perspective view of a disassembled lower member of the support arm of FIG. 16.

This head section 322b can be disassembled to an upper member 376a including the piston member 366, etc. and a lower member 376b including a housing portion of the disposal filter 344, etc. Namely, these upper member 376a and lower member 376b can be easily disassembled by unfastening and detaching bolts 378, 380, 382 and 384. FIG. 17 shows the lower member 376b thus disassembled. In this figure, reference numerals 386, 388, 390 and 392 are guide members for positioning the upper and lower members when the upper member 376a and the lower member 376b are connected to each other. A silicon seal 394 seals an upper portion of the disposal filter 344 in cooperation with the shutter member 358. This silicon seal 394 is positioned not to be shifted. The through hole 346 extends through the silicon seal 394 and the sealing chamber 348 is formed in a portion of the through hole 346 and an upper side portion of the disposal filter 344.

In FIG. 17, reference numerals 396 and 398 are guide plates of the retainer member 350 These guide plates 396 and 398 are respectively fixed to the lower member 376b by bolts 400, 402, 404 and 406 and can be easily detached from the lower member 376b by unfastening and detaching these bolts 400, 402, 404 and 406.

Figure 18:
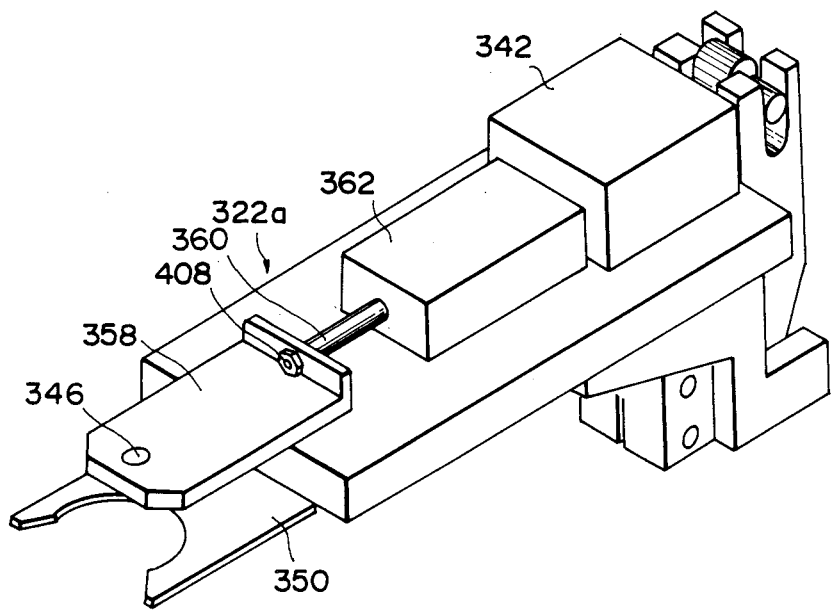
FIG. 18 is a perspective view of the remaining portion of the support arm when the head section of FIG. 16 is detached from the support arm.

FIG. 18 shows the remaining portion of the support arm member when the head section 322b in FIG. 16 is detached from the support arm member 322. In FIGS. 14 and 18, the shutter member 358 and the retainer member 350 are respectively fixed to the rods 360 and 352 by nuts 408 and 410. Accordingly, the shutter member 358 and the retainer member 350 can be easily detached from the support arm 322 by detaching these nuts 408 and 410.

As mentioned above, the head section 322b can be detached from the support arm member 322 by detaching the bolts, and can be thereby disassembled to the upper member 376a, the lower member 376b and guide plates 396 and 398. Further, the shutter member 358 and the retainer member 350 can be respectively detached from the support arm 322 by detaching the nuts. Accordingly, these detached members can be very easily cleaned As a result, the liquid attached to these members can be completely removed therefrom. Accordingly, there is no case in which the liquid attached to these members is mixed with a new liquid at the next filtering processing time and is solidified so that the shutter member 358 and the retainer member 350 are unoperated, etc.

Figure 19:
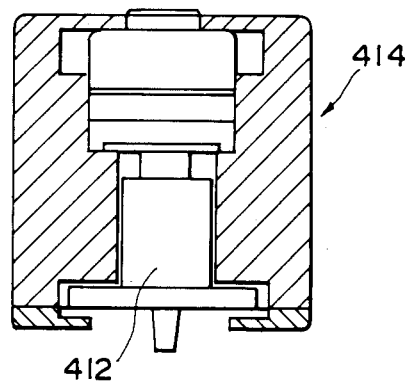
FIG. 19 is a cross-sectional view of the head section mounting another filter thereto.

Further, since the head section 322b can be detached from the support arm member 322, a head section of a different kind can be attached to the support arm meber 322. For example, in addition to the disposal filter using a filter paper as mentioned above, the head section can be constructed by a head section for attaching to the support arm, a disposal ultra-filter using an ultrafiltering film, a disposal solid phase container for extracting a solid phase using an enzyme or other filtering material, an other container for separation, and a container for separation, and a container combining these filters and the containers with each other. FIG. 19 shows a head section 414 attached to a disposal solid phase container 412 for extracting the solid phase. In accordance with the present invention, such head section can be very easily exchanged by the above-mentioned head section 322b.

Many widely different embodiments of the present invention may be constructed without departing from the spirit and scope of the present invention. It should be understood that the present invention is not limited to the specific embodiments described in the specification, except as defined in the appended claims.

What is claimed is:

1. An automatic preparation apparatus for automatically preparing samples comprising:
   turntable means in which a plurality of test tubes can be disposed in radial directions thereof;
   filter robot means for moving a removable filter onto one of said test tubes, said filter robot means having a support arm member for supporting the filter, said support arm member including a head part having a filter retainer means for releasably retaining the filter and a sealing means for forming a sealing chamber on a sample-injecting side of the filter, an arm part having an end tip portion connected to said head part and a rear end portion attached to a support post member, and means for detachably connecting said head part to said arm part;
   probe robot means capable of sampling a predetermined amount of liquid contained within said each one of the test tubes, and of injecting a predetermined amount of liquid into one of test tubes and into an injection port of said filter; and control means for controlling each of said means in accordance with a predetermined sequence to perform a desired preparation of the samples.

2. Apparatus as claimed in claim 1, wherein said turntable means comprises a turntable in which a plurality of groups of test tubes arrayed in one radial direction respectively can be arranged in a plurality of radial directions, and a drive means capable of turning said turntable in a horizontal plane.

3. Apparatus as claimed in claim 1, wherein said probe robot means comprises a probe needle the tip of which can be inserted into one of said test tubes and into the injection port of said filter, a microsyringe pump which can suck and discharge a predetermined amount of liquid via said probe needle, a horizontal drive means which can horizontally drive said probe needle, and a vertical drive means which can vertically drive said probe needle.

4. Apparatus as claimed in claim 3, wherein the apparatus comprises a cleaning means for cleaning said probe needle and said microsyringe pump, the tip of said probe needle being capable of being inserted into said cleaning means.

5. Apparatus as claimed in claim 3, wherein the apparatus can be coupled with a chromatography system, and wherein the apparatus has an input port for said chromatography system at a fixed position and the tip of said probe needle can be inserted into said input port.

6. Apparatus as claimed in claim 1 wherein said support post member has a drive means for turning said arm member in the horizontal plane such that an exit end of said filter can be located immediately above one of said test tubes.

7. Apparatus as claimed in claim 6, wherein said arm member comprises means for feeding compressed gas into said sealing chamber.

8. Apparatus as claimed in claim 6, wherein the apparatus comprises a filter supply unit for supplying unused filters and a discard box for discarding used filters, and wherein said drive means for said support post member turns said arm member such that said filter retainer means can be located immediately above said filter supply unit and discard box.

9. Apparatus as claimed in claim 6, wherein said arm member supported by said support post member so as to be turned in a horizontal plane comprises a drive means for turning said arm member by a predetermined angle in a vertical plane.

10. Apparatus as claimed in claim 1, wherein said control means comprises a microcomputer in which a sequence is programmed for achieving a desired preparation such that driving of said turntable means, filter robot means and probe robot means can be controlled in accordance with the instructions issued from said microcomputer.

11. Apparatus as claimed in claim 1, wherein one group of the test tubes comprises a sample tube, a dilution tube and a filtrate tube.

12. Apparatus as claimed in claim 1, wherein said filter is a disposable filter with an open-end type plastic housing having the injection port and an exit port, a diameter of said injection port being larger than a diameter of said exit port.

13. Apparatus as claimed in claim 12, wherein the diameter of the injection port of said housing is above 6 mm.

14. Apparatus as claimed in claim 12, wherein the ratio of the diameter of said injection port of said housing to that of said exit port is between 3:1 to 10:1.

* * * * *